(12) United States Patent
Boyd et al.

(10) Patent No.: US 10,660,588 B2
(45) Date of Patent: *May 26, 2020

(54) TUMOR TRACING DEVICE WITH MULTIPLE SCAN TUBES

(71) Applicant: Imatrex Inc., Las Vegas, NV (US)

(72) Inventors: Douglas P. Boyd, Las Vegas, NV (US); Larry Partain, Los Altos, CA (US); Samuel M. Song, Las Vegas, NV (US); Namho Kim, Las Vegas, NV (US); Roy E. Rand, Portola Valley, CA (US); Junghyun Kwon, Las Vegas, NV (US)

(73) Assignee: Imatrex Inc., Las Vegas, NV (US)

( * ) Notice: Subject to any disclaimer, the term of this patent is extended or adjusted under 35 U.S.C. 154(b) by 373 days.

This patent is subject to a terminal disclaimer.

(21) Appl. No.: 15/338,811

(22) Filed: Oct. 31, 2016

(65) Prior Publication Data

US 2017/0042489 A1    Feb. 16, 2017

Related U.S. Application Data

(63) Continuation-in-part of application No. 14/288,021, filed on May 27, 2014, now Pat. No. 9,801,594.

(60) Provisional application No. 61/827,359, filed on May 24, 2013, provisional application No. 62/248,830, filed on Oct. 30, 2015.

(Continued)

(51) Int. Cl.
*A61B 6/00* (2006.01)
*A61N 5/10* (2006.01)
(Continued)

(52) U.S. Cl.
CPC .......... *A61B 6/4021* (2013.01); *A61B 6/405* (2013.01); *A61N 5/1042* (2013.01);
(Continued)

(58) Field of Classification Search
CPC .... H05G 1/52; A61B 6/00; A61B 6/03; A61B 6/032; A61B 6/035; A61B 6/40;
(Continued)

(56) References Cited

U.S. PATENT DOCUMENTS 5,233,990 A  *  8/1993  Barnea .................. A61B 6/00
                                                    378/65
6,842,502 B2 *  1/2005  Jaffray ................. A61B 6/032
                                                    378/65

(Continued)

*Primary Examiner* — Anastasia Midkiff
(74) *Attorney, Agent, or Firm* — Workman Nydegger

(57) ABSTRACT

A system for tracking tumors during radiotherapy for interleaving treatment pulses with imaging pulses is disclosed. The system includes a plurality of multisource scanning eBeam X-ray tubes, each having multiple focal spots. The X-ray tubes are configured to emit X-rays in a plurality of different locations on a target by sequentially emitting the X-rays to the focal spots in the different focal spots. This is done such that the X-rays can be emitted to the plurality of different locations without substantially moving the X-ray tube or the target. The system further includes multiple imager panels configured to act as targets and configured to receive the X-rays from the focal spots of the X-ray tube. The system further includes a tomosynthesis reconstruction module configured to process outputs from the imager panels to construct a unified three-dimensional image that takes information from each of the different imager panels.

8 Claims, 11 Drawing Sheets

(51) Int. Cl.
*A61B 6/03* (2006.01)
*A61N 5/06* (2006.01)
*A61B 34/20* (2016.01)

(52) U.S. Cl.
CPC ......... *A61N 5/1049* (2013.01); *A61N 5/1067* (2013.01); *A61B 6/032* (2013.01); *A61B 34/20* (2016.02); *A61N 2005/0629* (2013.01); *A61N 2005/1061* (2013.01)

(58) Field of Classification Search
CPC ..... A61B 6/4021; A61B 6/4028; A61B 6/405; A61B 34/00; A61B 34/20; A61B 2034/2046; A61N 5/00; A61N 5/01; A61N 5/10; A61N 5/1042; A61N 5/1048; A61N 5/1049; A61N 5/1064; A61N 5/1065; A61N 5/1067; A61N 5/1077; A61N 5/1084; A61N 2005/0626; A61N 2005/0629; A61N 2005/0632; A61N 2005/1061; A61N 2005/1092
See application file for complete search history.

(56) References Cited

U.S. PATENT DOCUMENTS

| | | | | |
|---|---|---|---|---|
| 6,876,724 B2* | 4/2005 | Zhou | ...... | A61B 6/032 378/119 |
| 7,245,698 B2* | 7/2007 | Pang | ...... | A61B 6/025 378/22 |
| 7,519,151 B1* | 4/2009 | Shukla | ...... | A61B 6/025 378/62 |
| 7,567,647 B1* | 7/2009 | Maltz | ...... | A61B 6/025 378/21 |
| 7,936,858 B2* | 5/2011 | Hashemi | ...... | A61B 6/025 378/21 |
| 8,515,004 B2* | 8/2013 | Star-Lack | ...... | G01N 23/046 378/21 |
| 8,530,549 B2* | 9/2013 | Tanimoto | ...... | B62D 55/244 524/435 |
| 9,801,594 B2* | 10/2017 | Boyd | ...... | H01J 37/147 |
| 2004/0208276 A1* | 10/2004 | Kaufman | ...... | A61B 6/032 378/4 |
| 2007/0081623 A1* | 4/2007 | Eilbert | ...... | G01N 23/2252 378/10 |
| 2009/0080604 A1* | 3/2009 | Shores | ...... | A61B 6/032 378/37 |
| 2010/0166144 A1* | 7/2010 | Boyd | ...... | A61N 5/1049 378/62 |
| 2011/0080990 A1* | 4/2011 | Filiberti | ...... | A61N 5/1049 378/4 |
| 2012/0163531 A1* | 6/2012 | Zhang | ...... | A61B 6/025 378/9 |
| 2012/0230462 A1* | 9/2012 | Robar | ...... | A61N 5/1049 378/4 |
| 2012/0300901 A1* | 11/2012 | Lewalter | ...... | A61B 6/4028 378/22 |

* cited by examiner

Typical Diagram Motion During Two SABR Radiation Delivery Fractions A and B

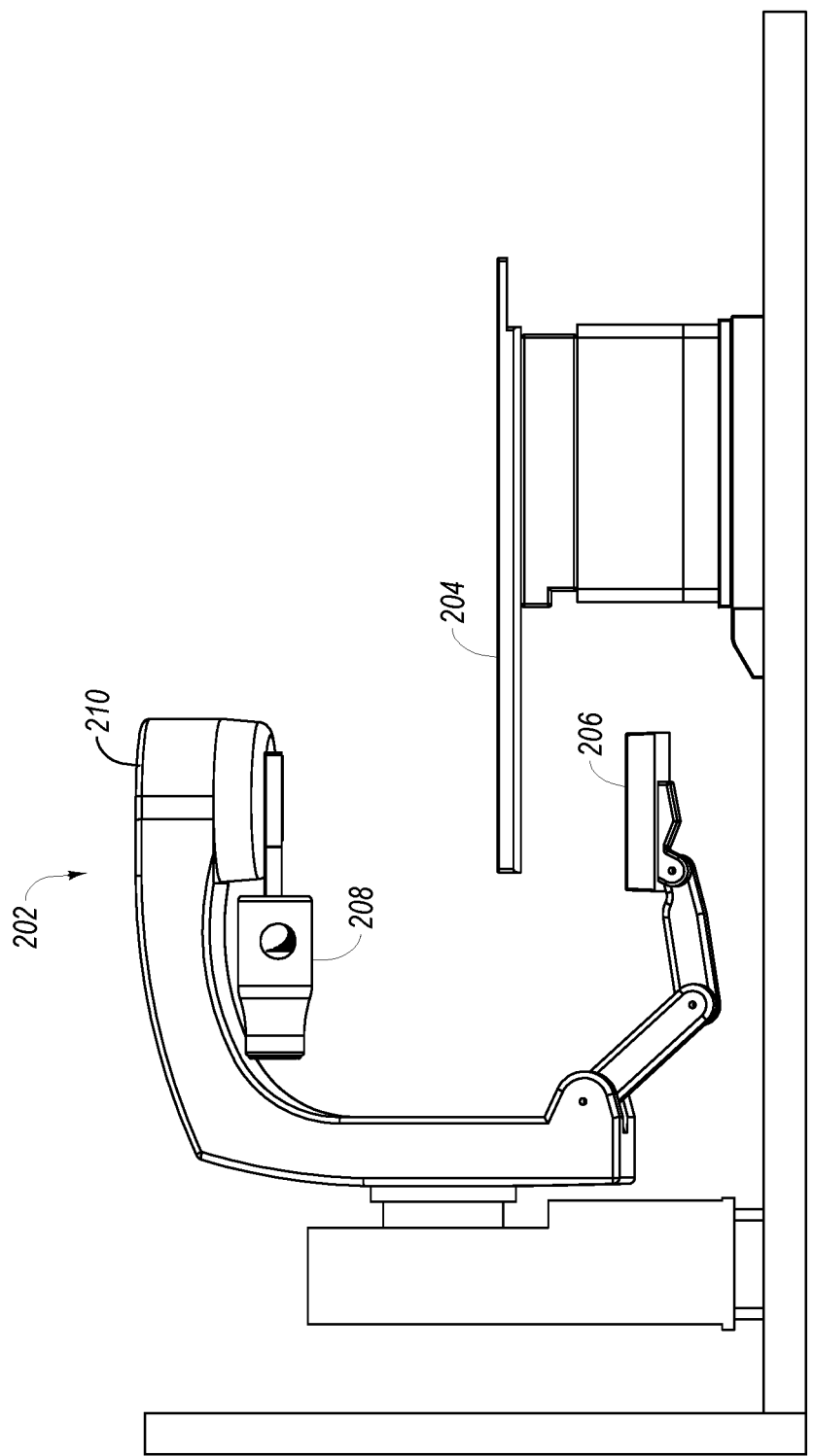

| Acquire 19 kV Projection Images (kV) (40 ms readout + dwell of 7ms each) (0.89s) | Deliver MV Treatment Pulses (0.96s) | Reset For kV Imaging (0.07s) |
|---|---|---|

1.92 s Cycle Time (0.52cycles/s)

TUMOR TRACING DEVICE WITH MULTIPLE SCAN TUBES

CROSS-REFERENCE TO RELATED APPLICATIONS

This application is a continuation-in-part of U.S. patent application Ser. No. 14/288,021, entitled "EBEAM TOMOSYNTHESIS FOR RADIATION THERAPY TUMOR TRACKING," filed on May 27, 2014, which application claims the benefit of and priority to U.S. Provisional Patent Application Ser. No. 61/827,359 filed on May 24, 2013 and entitled "EBEAM TOMOSYNTHESIS FOR RADIATION THERAPY TUMOR TRACKING." This application further claims priority to and the benefit of U.S. Provisional Patent Application No. 62/248,830, filed on Oct. 30, 2015, entitled "TUMOR TRACING DEVICE WITH MULTIPLE SCAN TUBES." Each of the above-listed applications is expressly incorporated herein by reference in its entirety.

BACKGROUND

Background and Relevant Art

Lung cancer is a major health problem. Every year, more people in the U.S. die from lung cancer than from prostate, breast, colon and rectum cancers combined. Stereotactic body radiation therapy (SBRT) is a highly successful non-invasive alternative to surgery for localized lung tumors, with local control rates reported to be 80% to 90%. Early reports of high normal tissue toxicities following SBRT (i.e. normal healthy tissue being exposed to tissue destroying radiation) have led to empirically-derived limits on radiation dose metrics and target size. However, these restrictions limit the number of patients that are eligible for SBRT. Often, the tumor itself is small enough for safe treatment, but the treated volume exceeds the safely treatable limit due to the addition of clinical safety margins to account for random and systematic motions. In addition, recent studies have shown that lung tumor motion during radiotherapy cannot be reliably predicted from pretreatment imaging. Direct in-treatment imaging of lung tumors to ensure proper radiation targeting and healthy tissue avoidance is an unsolved challenge.

The subject matter claimed herein is not limited to embodiments that solve any disadvantages or that operate only in environments such as those described above. Rather, this background is only provided to illustrate one exemplary technology area where some embodiments described herein may be practiced.

BRIEF SUMMARY

One embodiment illustrated herein includes a method that includes acts for tracking tumors during radiotherapy for interleaving treatment pulses with imaging pulses. The method includes emitting an eBeam to a plurality of focal spots on an X-ray tube to emit X-rays in a plurality of different locations on a target by sequentially emitting the X-rays to the focal spots in the plurality of focal spots. This is done such that the X-rays can be emitted to the plurality of different locations without substantially moving the X-ray tube or the target. The method further includes detecting signals from the X-rays at the target. Using the signals, an image is constructed.

Another embodiment includes a system for tracking tumors during radiotherapy for interleaving treatment pulses with imaging pulses. The system includes a multisource scanning X-ray tube having a plurality of focal spots. The X-ray tube is configured to emit X-rays in a plurality of different locations on a target by sequentially emitting the X-rays to the focal spots in the plurality of focal spots. This is done such that the X-rays can be emitted to the plurality of different locations without substantially moving the X-ray tube or the target. The system further includes an imager panel configured to act as the target and configured to receive the X-rays from the focal spots of the X-ray tube. The system further includes a tomosynthesis reconstruction module configured to process output from the imager panel to construct an image.

Another embodiment includes a system for tracking biological features during radiotherapy. The system includes a first multisource scanning X-ray tube that has multiple focal spots. The first X-ray tube is configured to emit X-rays in multiple different locations on a first target by sequentially emitting the X-rays to the focal spots in the plurality of focal spots. As such, the X-rays can be emitted to the different locations without substantially moving the first X-ray tube or the first target. The system further includes a first imager panel configured to act as the first target for the first X-ray tube, where the first imager panel receives the X-rays from the focal spots of the first X-ray tube.

The system also includes a second multisource scanning X-ray tube that has multiple focal spots. The second X-ray tube is configured to emit X-rays in multiple different locations on a second target by sequentially emitting the X-rays to the focal spots in the plurality of focal spots. Still further, the system includes a second imager panel configured to act as the second target for the second X-ray tube, where the second imager panel receives the X-rays from the focal spots of the second X-ray tube, and a tomosynthesis reconstruction module configured to process output from the first and second imager panels to construct a unified three-dimensional image that takes information from both the first and the second imager panels.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages will be set forth in the description which follows, and in part will be obvious from the description, or may be learned by the practice of the teachings herein. Features and advantages of the invention may be realized and obtained by means of the instruments and combinations particularly pointed out in the appended claims. Features of the present invention will become more fully apparent from the following description and appended claims, or may be learned by the practice of the invention as set forth hereinafter below.

BRIEF DESCRIPTION OF THE DRAWINGS

In order to describe the manner in which the above-recited and other advantages and features can be obtained, a more particular description of the subject matter briefly described above will be rendered by reference to specific embodiments which are illustrated in the appended drawings. Understanding that these drawings depict only typical embodiments and are not therefore to be considered to be limiting in scope, embodiments will be described and explained with additional specificity and detail through the use of the accompanying drawings in which:

FIG. 2B illustrates an alternate view of a radiotherapy system;

DETAILED DESCRIPTION

Figure 1A:
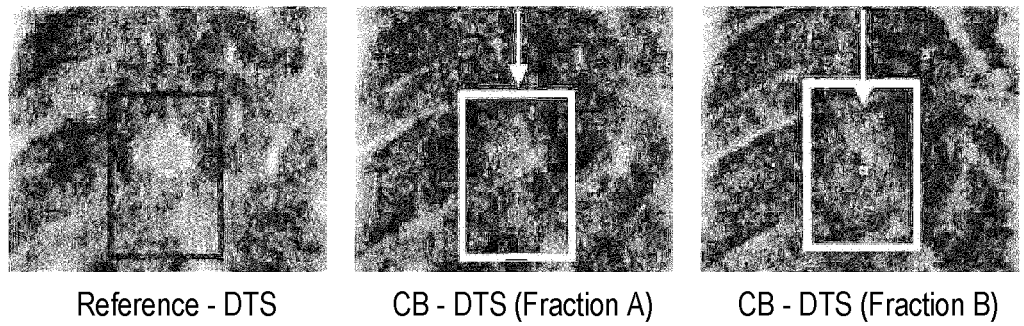
FIG. 1A illustrates shifting of a tumor.
Figure 1B:
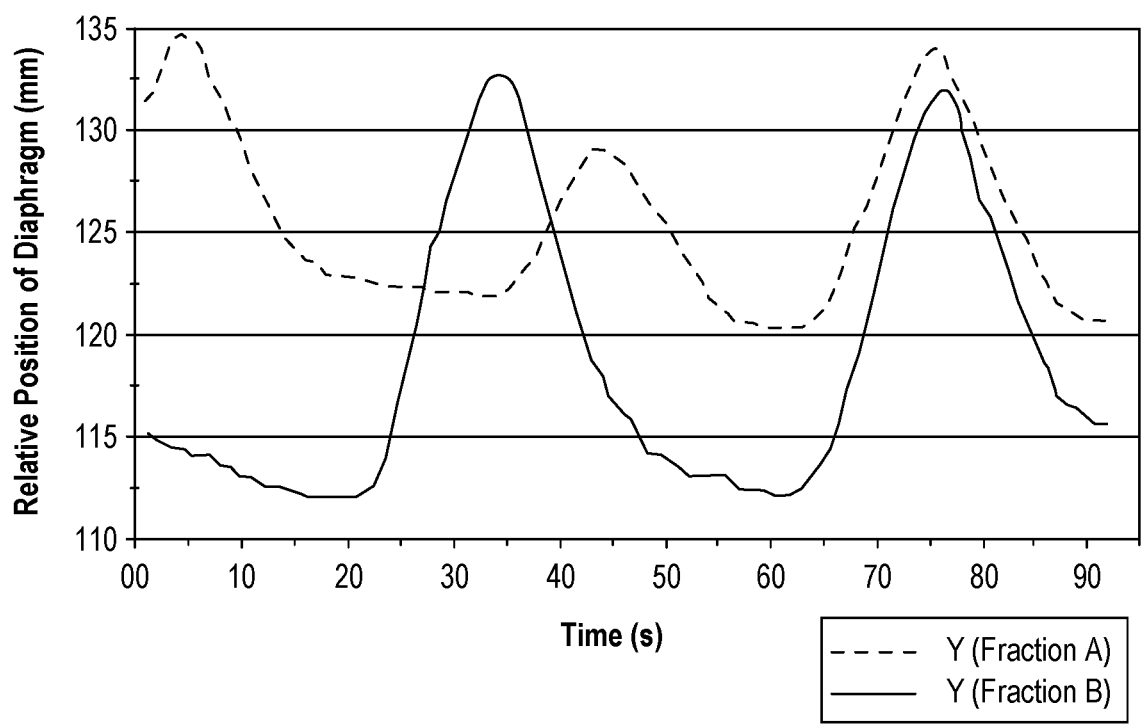
FIG. 1B illustrates a graph showing diaphragm motion.

Embodiments of the invention may implement methods and/or systems for achieving synchronized image guided stereotactic body radiation therapy (SIG-SBRT) or synchronized image guided stereotactic ablative radiotherapy (SIG-SABR). Here SIG-SBRT and SIG-SABR implement the same types of methods and systems. Typically the margins of treatment delivery are adjusted wide enough to accommodate any respiratory motion of a lung tumor. Lung tumor motion is largely driven by diaphragm motion as illustrated in FIGS. 1A and 1B. As illustrated in FIG. 1B, the diaphragm peaks are inspiration and the troughs are expiration where the latter have a lot less motion. The distance between peaks in seconds and their amplitudes in millimeters varies along with base line position shifts. Thus, it can be important to monitor respiratory motion of tumor positions accurately for every breath and for every fraction of treatment dose delivered. Otherwise significant portions of healthy surrounding lung tissue and bone are needlessly damaged by the heavy radiation treatment dose intended only for the malignant tumor itself. Note, in FIG. 1A, the relative position shift of the center of the tumor (the dot) relative to the ribs in Fraction A versus Fraction B.

Figure 2A:
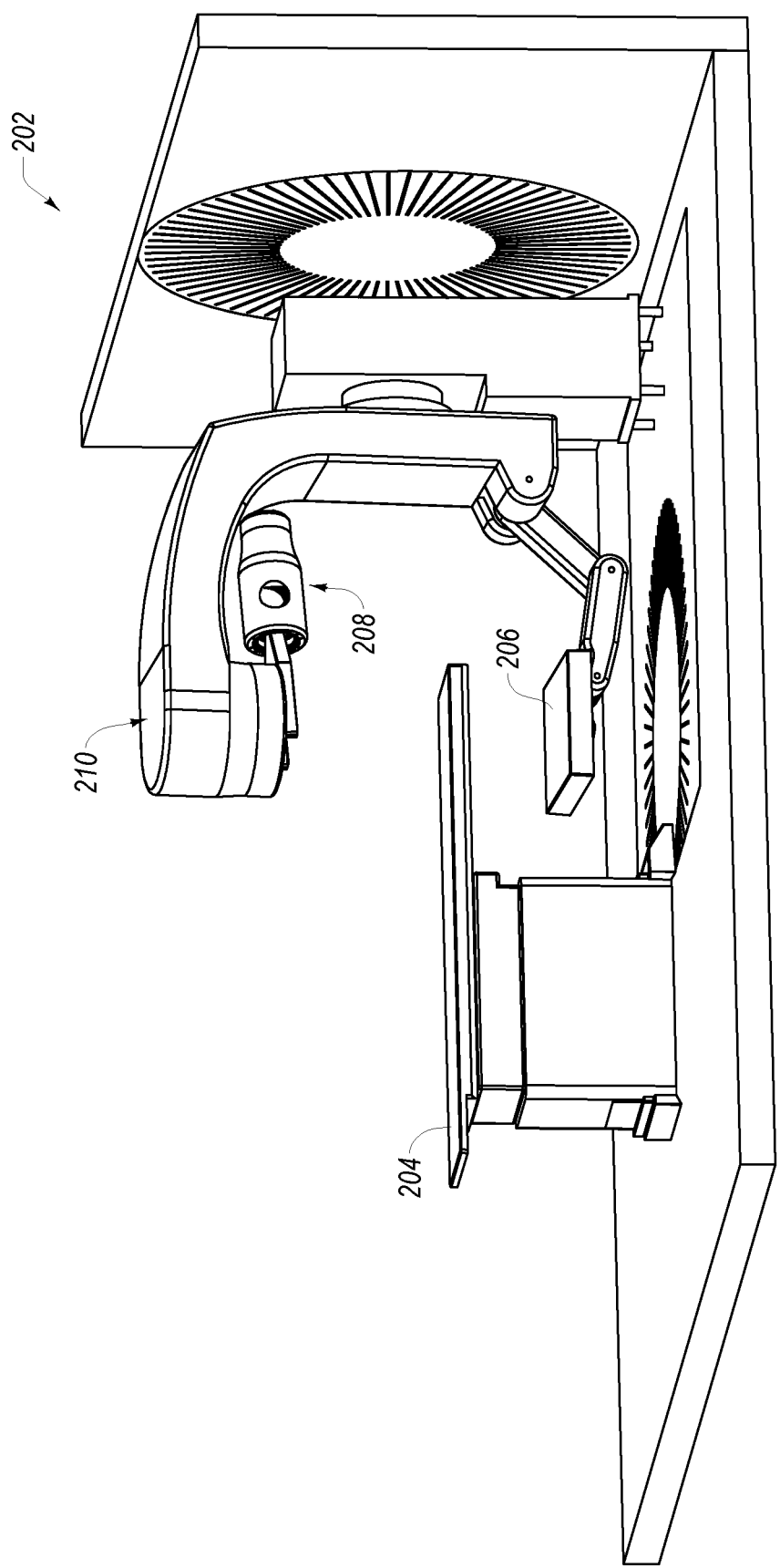
FIG. 2A illustrates an example of a radiotherapy system.

One system that enables the new SIG-SBRT method is illustrated in FIGS. 2A and 2B. A standard rotating C-arm MV linac radiotherapy system 202 is shown with its patient positioning support table 204. A portal X-ray imager panel 206 is opposite a gantry treatment head 210 to help monitor the patient and tumor positions for set up and during treatment. The illustrated embodiment can be conceptualized as a standard MV portal imager but, turned upside down to convert it into a universal kV-MV portal imager. Embodiments may also include a kV multi-source X-ray tube 208 mounted directly under the MV linac gantry treatment head 210.

As shown in FIGS. 3A, 3B 3C, and 3D, the X-ray tube 208 has a squared "U" shaped head 212 surrounding the MV linac treatment beam and provides 19 (or some other appropriate number) kV X-ray focal spots (e.g. one focal spot is called out at 214) that illuminate the universal portal imager in the same beams-eye-view (BEV) as the MV treatment beam.

In the illustrated example, the portal X-ray imager panel 206 may be implemented using a flat panel detector available from Varian Medical Systems of Palo Alto, Calif. FIGS. 3A, 3B 3C, and 3D show one example design of a U-shaped eBeam scan tube for the tumor tracking project assuming a conventional radiotherapy gantry system 202 and the Varian portal detector. The X-ray tube head 212, in this example, is similar in size to the imager panel in that it has dimensions of 30 cm×30 cm and as such is a bit smaller than the Varian MV-kV flat panel detector implemented as the imager panel 206 which is 30 cm×40 cm. This geometry provides a two dimensional scan with a typical tomographic angle of 26 degrees depending with the Source to Detector Distance (SSD) at approximately 150 cm. The electron gun and deflection system may be configured using components that operate at 180 kV. Such an electron gun could be made using suitable parts from L-3 Communications electron devices division. However, this is somewhat longer and larger than what is required here, 120 kV. This part may be a sealed system without active vacuum pumping and contains a mod-anode that serves as a grid for current control. Some embodiments may implement a lighter and more compact system for 130 kV.

The X-ray target of this tube is U-shaped with about an 8-10 degree target angle with respect to the flat panel detector 206 so that the length of the focal spot is shortened by a large factor. The target is made of water cooled copper with thin tungsten braised on the surface. Additional water cooling channels cool the X-ray window and nearby vacuum chamber walls. The eBeam focal spot on the target is in the range of about a 1 mm by 10 mm ellipse for an effective focal spot size of approximately 1 mm FWHM. Beam focusing and steering can be accomplished using a deflection system that employs a solenoid, x-y dipoles, and x-y quadrupoles. An X-ray tuning system is used for beam alignment.

The three straight lengths of the target, in the illustrated example, each have 6 target positions, and with two additional target positions near the two corners, embodiments may have a total of about 20 tomographic views (19 to be precise in the illustrated example). Each target position has an associated collimator to block X-ray paths that fall outside the flat panel detector panel to minimize both patient exposure and scattered radiation. Some embodiments may implement one or more vane collimators inside the vacuum chamber.

Figure 3A:
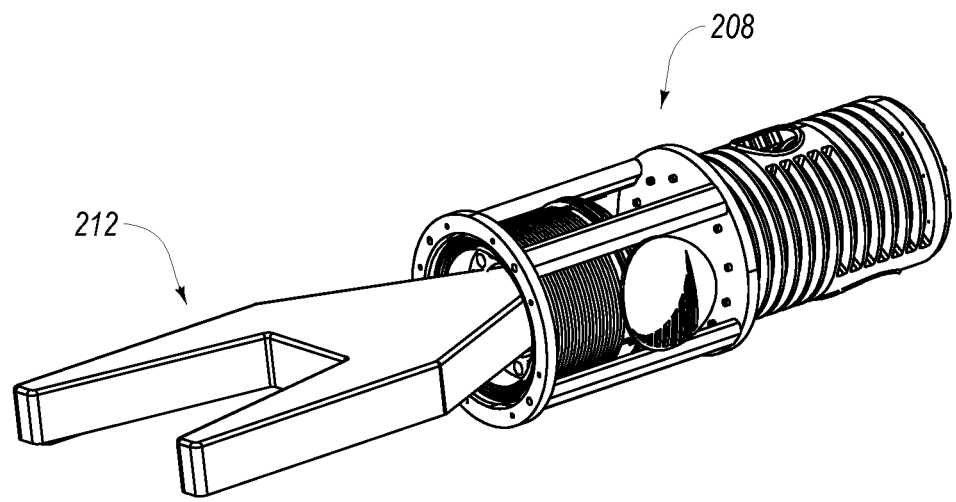
FIG. 3A illustrates an example of an X-ray tube.
Figure 3B:
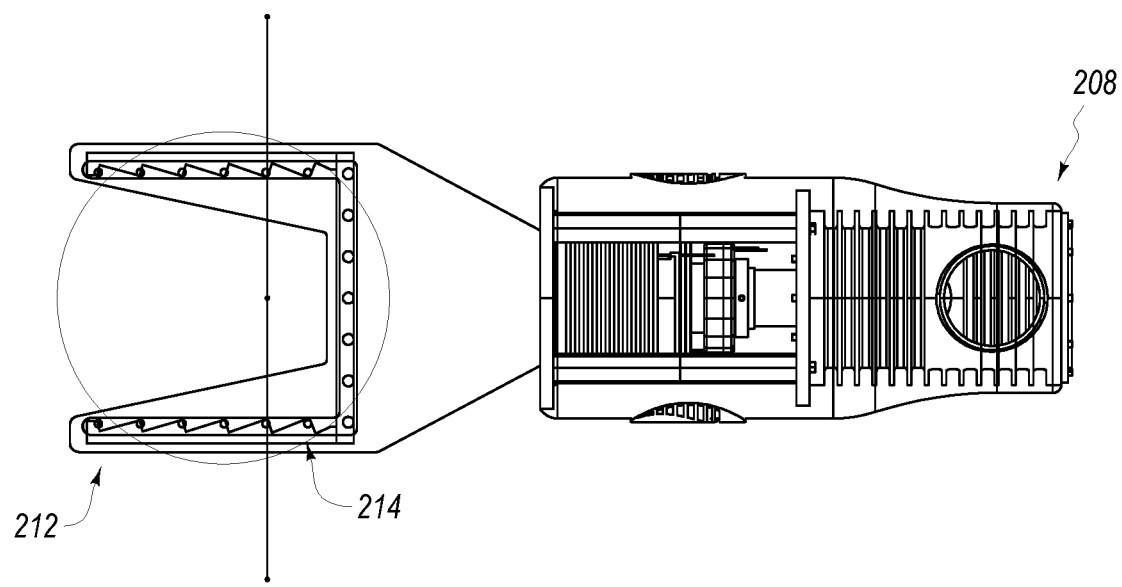
FIG. 3B illustrates an alternate view of the X-ray tube.
Figure 3C:
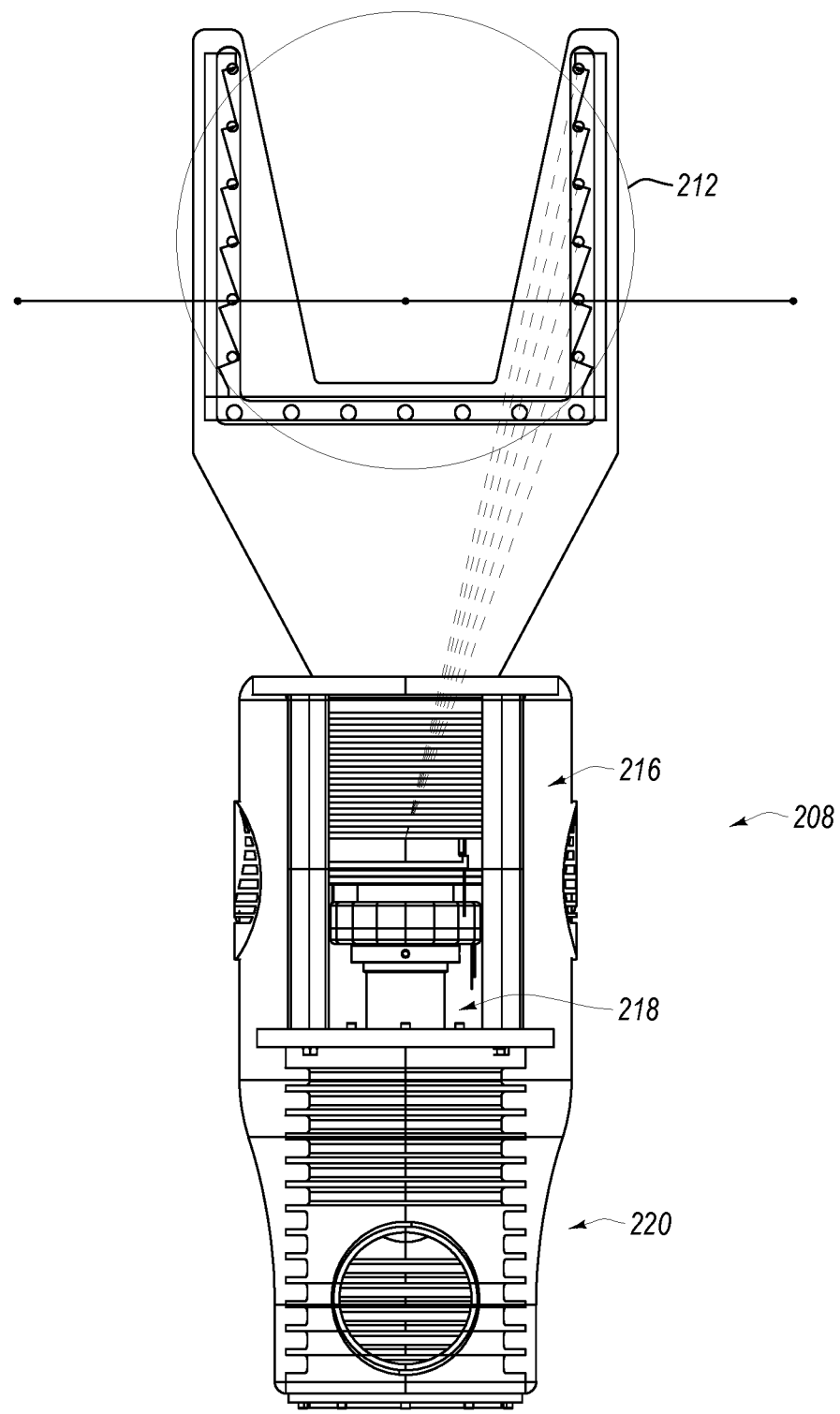
FIG. 3C illustrates yet another alternate view of the X-ray tube.

FIG. 3C illustrates 3D details of the target design and collimator design. This design has 19 target positions. Starting from the top, there is the U configuration of targets and collimator holes. At the center are deflection coils 216 including dipoles, quadrupoles, and a solenoid 218. At the bottom is an electron gun source 220 operating at 50 mA and 130 kV. The gun current is turned on and off using a mod anode.

The kV multi-source X-ray tube 208 is capable of operating at power levels of 100 mA or higher at up to 180 kV with a duty factor of 50% or higher. However, the portal X-ray imager panel 206 used for imaging is able to operate in the path of the MV treatment beam and recover quickly from saturation produced by MV treatment pulses. For example, the performance of the presently available Varian MV-IN flat panel detector available from Varian Medical Systems of Palo Alto, Calif. limits the speed of the system today to about 2 sec sampling.

Based on various scientific studies and observations, it appears that 10 mAs is sufficient for a high diagnostic quality tomogram of the chest. Further, about 20 views appears to be sufficient, therefore each view would be at about 0.5 mAs. Additionally, applying compressed sensing a further factor of about 10 is feasible.

Some embodiments of the invention can produce near-CT-quality images in planes through the treatment region that are transverse to the therapy beam. Therefore, embodiments can provide real time adjustments to the (multi-leaf collimator) MLC that adjusts the cross section of a therapy beam used applied to a tumor to better conform to the tumor outline (focus treatment beam on the tumor). If the tumor is moving, as is typical in lung cancer, the adjustments will be made in real time during a rotational therapy procedure. This will enable a substantial reduction in the volume of healthy tissue (the margins) that is exposed to radiation thus reducing the volume of non-malignant necrosis.

As illustrated above a unique kV multi-source X-ray tube 208, which is a scanning electron beam tube that provides rapid switching of an X-ray focal spot in sequence from 19 target sites (or some other appropriate number) positioned along three sides of a square is implemented. This arrangement of focal spots nearly surrounds the MLC near a therapy radiation head 210. A collimator system comprising a tantalum plate with machined apertures just below the targets collimates the X-ray beams such that the universal kV-MV imager 206 can receive each of the 19 projection images in sequence. Since the array of focal spots is offset, the projection images will expose only ½ or less of the rows of pixels in the imager as the projection image moves to different sub-regions on the panel. The readout time for kV imaging on the available imagers is typically 40 msec to 80 msec for the full panel using 2×2 pixel binning. Since only half of the panel need be readout, the readout time per projection image can be reduced to about 20 msec in some embodiments. Prior to reading out, the panel will be exposed to X-rays from a 87 mA, 130 kV electron beam (or other appropriate electron beam) directed on an inclined, water-cooled, tungsten target focused to an effective focal spot size of about 1.4 mm full-width half maximum (FWHM). As noted above the beam can be formed and steered using an X-ray tube that includes components originally developed at Imatron, Inc. for cardiac EBCT, but later improved at L-3 Communications for the development of an airport luggage scanner. The multi-source e-beam X-ray tube is a baked and sealed system maintained with a small electronic Vac-Ion pump.

A unique feature of the universal kV-MV imager 206 is its ability to also record images from the therapy beam. This is feasible since the normal MV copper buildup plate can be placed on the back side of the imager 206, and a forward bias applied to clear a prior image from MV therapy beam exposure in a time interval of 75 msec, for high sensitivity kV imaging, that includes non-linear lag corrections. Although currently available kV-MV imagers with these features are smaller (30 cm×40 cm), larger MV hardened panels for MV imaging of up to 43 cm×43 cm are available and future modifications for dual kV-MV use are feasible.

The basic design parameters for one example system are presented in the table below:

| Specifications | Estimated result | Notes |
| --- | --- | --- |
| X-ray power | 11.6 mAs | 130 kV, 87 mA, 7 msec dwell time, 1.4 mm focal spot size (FWHM), 19 focal positions per scan, 0.6 mAs per spot |
| Resolution | Contour determination estimated at ±1 mm | 20 1-cm thick slices with 200 × 200 1 mm pixels per slice |
| kV image acquisition time | 513 msec | 27 msec for readout of partial area of panel for each spot (20 msec for readout of half of the panel + 7 msec dwell time) |
| Reconstruction time | 200 msec | Iterative reconstruction on GPU followed by tumor contour determination. The MLC will contribute additional latency but can be pre-adjusted by predictive techniques during kV acquisition. |
| Repetition rate | 1 volume image/sec | This assumes 487 msec is used for radiotherapy which is a duty factor of 49%. |
| Tomographic angle | 26° to 32° | Source to isocenter = 64.2 cm, Isocenter to detector = 40 cm, Detector panel size = 43 cm × 43 cm |

Imager Panel

The Varian MV-kV flat plate imager has the following characteristics:

| Property | Spec | Comment |
| --- | --- | --- |
| Readout Time | 67 msec | 15 frames/s |
| Recovery after MV pulse | 67 msec | |
| DQE | 50% | |
| Resolution | .8 × .8 mm pixels | Based on 2 × 2 |
| Size | 30 × 40 cm | |

The system illustrated can be used to acquire images and deliver treatment pulses to a patient. In particular, embodiments may interleave MV pulses (e.g. from an appropriate radio therapy source, such as a linear accelerator, gamma sources, proton sources, carbon ions, etc. in the treatment head 210) and kV pulses (e.g. from the multisource scanning X-ray tube). Since the recovery time from an MV pulse is relatively long, embodiments may implement a gating scheme with time for MV pulses and kV pulses shared at 50%. Since, in one example embodiment, it will take 20*67 msec=1.34 s to gather about 20 views of kV data, the MV pulsing could be on for about 1 sec followed by about 0.067 recovery and about 1.34 sec of kV imaging. Thus there would be a new tomographic image every 2.4 seconds. The kV imaging readout time could also be speeded up by ×2 reading a reduced area of the portal detector or by summing more pixels, say 3×3 rather than 2×2. In this case performance would be faster as shown. The following table illustrates various detector modes and timing for some embodiments of the invention:

| Detector Mode | kV speed | MV pulsing (s) | MV recovery (s) | kV pulsing (s) | Total Latency (s) | MV duty factor |
|---|---|---|---|---|---|---|
| Standard Mode | 15/s | 1 | .067 | 1.34 | 2.4 | .42 |
| 2X Mode | 30/s | .5 | .067 | .67 | 1.24 | .40 |
| 3X Mode | 45/s | .45 | .067 | .45 | 0.97 | .46 |
| 6X Mode | 90/s | .23 | .067 | .23 | 0.53 | 0.43 |

This table can be easily adjusted to make the MV duty factor in the range of 40-50% in order to reduce the impact on total treatment time. To achieve latency in the 1 sec range may require a 2-3× speed up of the kV readout. It should be noted that the MV duty factor will in many cases extend the length of time for the therapy treatment.

Figures 3D, 4:
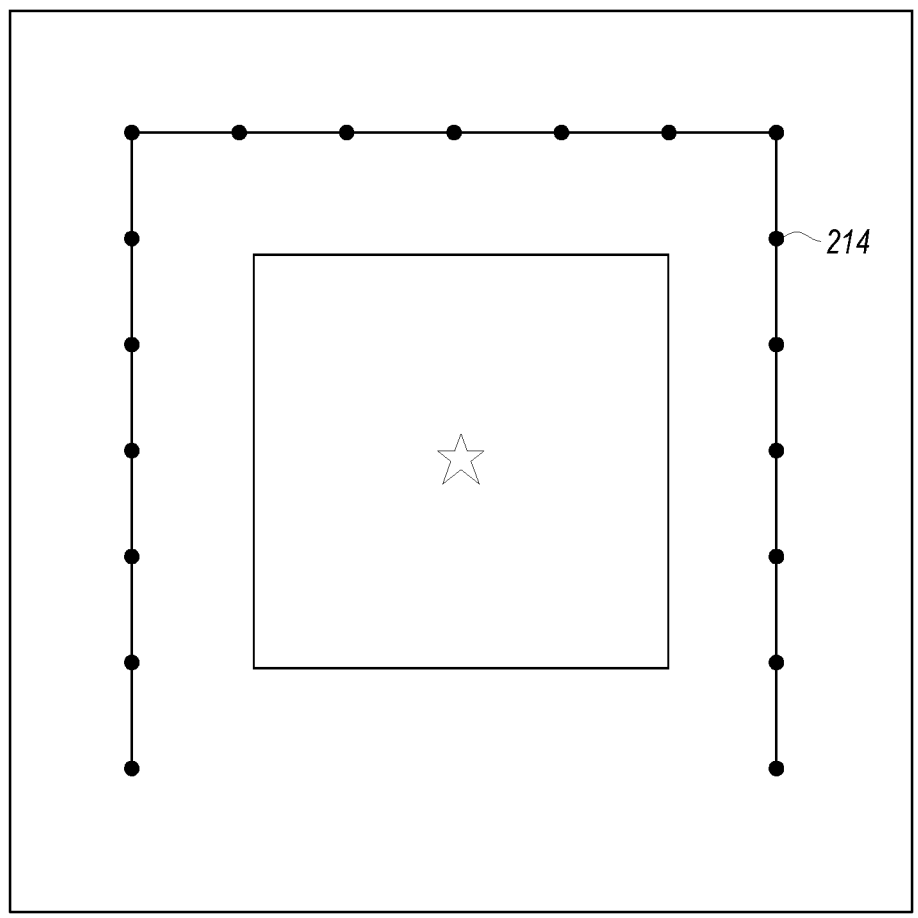
FIG. 3D illustrates a representation of target locations on the X-ray tube.
FIG. 4 illustrates a timing diagram showing timing for actions in a treatment scenario.

In one example embodiment, 19 kV projection images are promptly reconstructed into digital tomosythesis (DTS) images of the lung using a tomosythesis reconstruction module. Such a module may include various computer hardware and logic (such as programmatic or hardware means) to construct appropriate images as explained in more detail below. An example, of the time sequencing of this whole tracking and MV treatment delivery process is summarized in FIG. 4. In particular, FIG. 4 illustrates a 1.92 s cycle time. FIG. 4 illustrates that embodiments acquire 19 kV projection images where each image is performed with a 40 ms readout, plus a 0.7 ms dwell for a total of about 0.89 seconds for all 19 images. MV treatment pulses are delivered for about 0.96 seconds, and a reset for kV imaging is performed for about 0.070 seconds, for a total of about 1.92 seconds per cycle.

The 0.89 s of 19 kV projection image acquisition is synchronized to lie during the least motion, exhale portion of the respiratory cycles shown in FIG. 1B and the 0.96 s fraction dose delivery is synchronized for the next following exhale portion of the cycle to achieve most accurate delivery of a dose centered on the tumor itself. Should an exhale portion occasionally become too short, the kV acquisitions and/or the fraction treatment deliveries can be split between two or more adjacent exhale portions of the cycles. The much larger intensities of the MV treatment beams use a 0.07 s forward bias reset of the universal imager to regain the lower sensitivity needed for the next following kV image acquisition.

Some embodiments have a system latency of about 0.21 s for the multi-leaf collimator of the linac radiotherapy system to adjust its fingers to deliver the fraction dose shape to a new position of the tumor determined by the latest kV DTS image data set. The time between exhales is sufficient to accommodate this multi-leaf collimator repositioning. If the patient respiratory rate changes significantly the dose fraction delivery can be delayed until respiration returns to typical levels. This is what is meant as used herein by "respiratory synchronized image guided SBRT or SABR."

The "Beam's Eye View" (BEV) configuration described above may offer, in some embodiments, at least two innovative benefits. First, DTS volume reconstruction produces relatively poor resolution in the axial dimension, or the direction perpendicular to the motion of the source. Using the BEV configuration, this axis is coincident with the therapy beam axis, and resolution in this direction is not important. Thus an advantage that may be achieved using the BEV geometry is that the resulting tomograms are automatically aligned with the plane of the collimator and its 2-D beam profile impinging on the tumor outline. This alignment is not available using the usual onboard fluoroscopy system that is normally positioned at a large angle to the therapy beam axis. Second, the reconstructed tomograms will have the same physical alignment as the portal MV projection image, and thus will provide a detailed record, or even real-time feedback of the therapy beam profile with respect to the tumor profile at each gantry angle.

Assuming the X-ray technical factors and timing factors as illustrated above in the example table, a few complete system options may be implemented as follows:

| Detector mode | Detector readout time (msec) | Latency (s) | mA at 130 kV | kV pulse length per view (msec) | kV duty factor | Comments |
|---|---|---|---|---|---|---|
| Standard | 67 | 2.4 | 50 | 10 | .08 | Based on 15/s performance and .067 recovery for today's system |
| 2X | 33 | 1.24 | 50 | 10 | .16 | |
| 3X | 22 | .97 | 50 | 10 | .21 | |
| 6X | 11 | .53 | 50 | 10 | .37 | |

In these modes the eBeam scan tube 208 has grid control enabling shutting down the beam current between pulses. In between pulses the deflection system moves the beam position to the next of about 20 focal spots (in the illustrated example, 19) on the U-track.

The detector performance has little to do with the instantaneous heating of tungsten. Since the tungsten is water cooled, there is typically 0.53-2.4 sec between pulses at the same source spot, which will give ample time for cooling. In this system, water cooling may include cooling of the region around the X-ray window and surrounding vacuum chamber to remove heat due to back scattered electrons in addition to the target.

A further factor of 10 reduction in cooling is feasible based on Compressive Sensing (CS) algorithms, but at a cost of more GPU computing requirements. Part of this factor of 10 will be for abdomen-pelvis imaging due to the greater attenuation in this part of the body as compared to the chest.

It is desirable that the kV radiation exposure be a small fraction of the treatment exposure. Using an X-ray mAs that is 2.3 times an AP chest exposure, and a AP chest skin dose that is 0.04 mSv, embodiments may exhibit approximately 0.1 mSv for each complete scan. Thus the procedure dose will be as follows:

| Detector Mode | Treatment time of 1 min (mSv) | Treatment time of 2 min (mSv) |
|---|---|---|
| Standard | 2.5 | 5 |
| 2x | 4.84 | 9.68 |
| 3X | 6.2 | 12.4 |
| 6X | 11.3 | 22.6 |

Given that the therapy exposure is in the range of 4000-8000 mSv, all of these exposures are well within 1% of treatment exposure.

In conventional tomosyntheis, reconstruction is performed by simple backprojection, sometimes referred to a step and add. However some embodiments use an advanced algorithm based on the theory of Compressive Sensing (CS) Framework. For example, embodiments may use the algorithm described in Andersen, A. H., and A. C. Kak. "Simultaneous algebraic reconstruction technique (SART): a superior implementation of the ART algorithm." Ultrasonic imaging 6.1 (1984): 81-94 or Sidky, Emil Y., et al. "Enhanced imaging of microcalcifications in digital breast tomosynthesis through improved image-reconstruction algorithms." Medical physics 36.11 (2009): 4920-4932, both of which are incorporated herein by reference in their entireties.

Further CS optimizes the signal to noise in the final image enabling dose reduction (or mAs) reduction of up to a factor of 10. However, the CS methods involve iterative reconstruction that is demanding on computer resources. Some embodiments may implement the algorithm on graphical processing unit (GPU) boards which have more than 2000 processors in parallel, and using a small array of these boards embodiments can achieve volume tomosynthesis reconstruction times in the fractions of a second. Further, embodiments may implement fast image segmentation of this GPU array, and the image segmentation will enable fast boundary detection to be delivered to the multi-leaf collimator system of the radiotherapy gantry. In particular, some embodiments may use NVidia GPU cards for image reconstruction as part of the tomosynthesis reconstruction module, in place of other computing system computer. Algorithms may be coded using CUDA, the native language for NVidia GPUs or OpenCL available from khronos.org.

Figure 5:
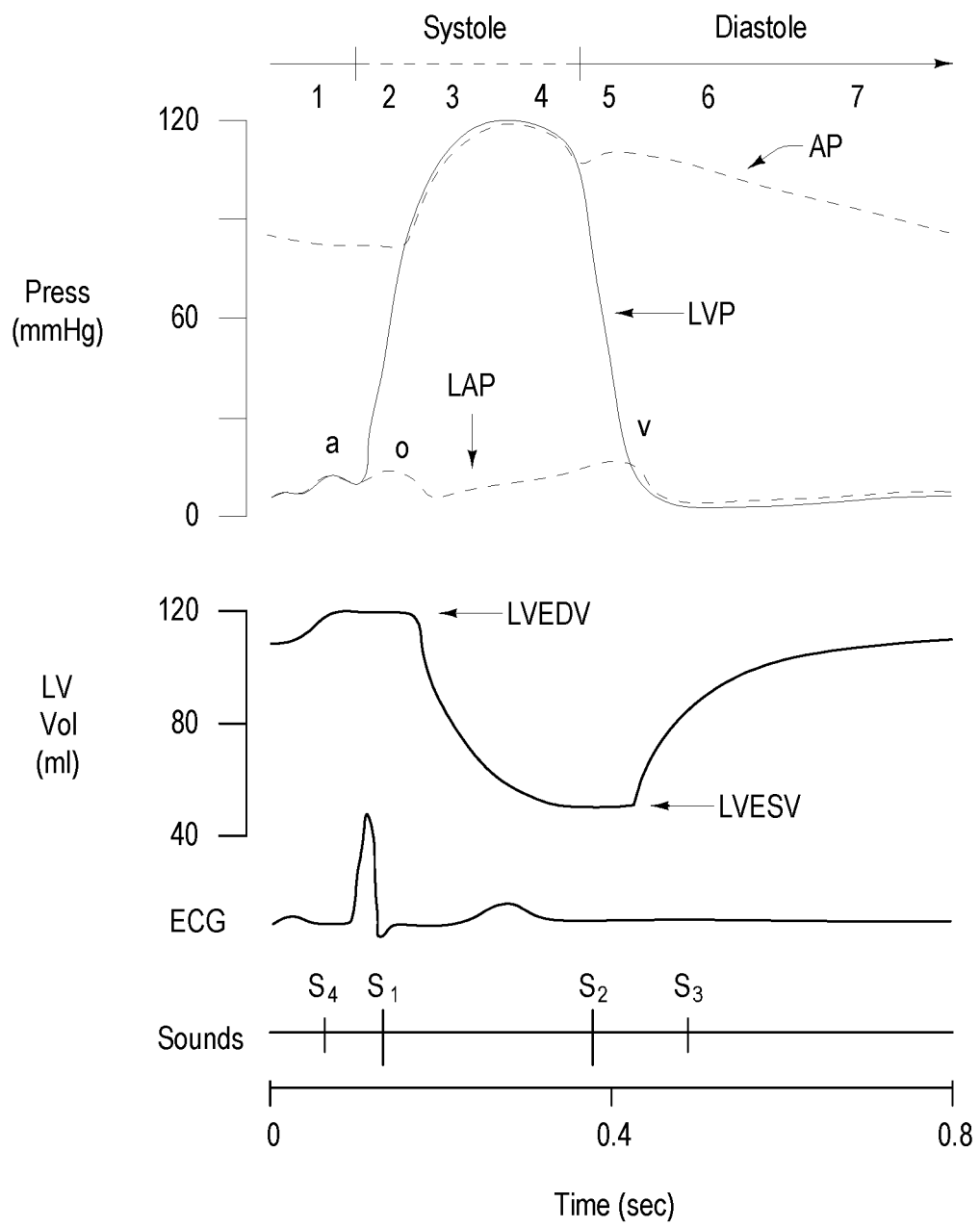
FIG. 5 illustrates a representative cardiac cycle.

One alternate embodiment adds cardiac synchronization to SIG-SBRT and SIG-SABR. The normal resting heart rate is 60 to 100 beats per min. This corresponds to a heartbeat every 0.6 to 1.0 s. A representative cardiac cycle is shown in FIG. 5. The minimum heart beat driven motion of lung tumors is during the Regions 1, the last half of 6 and 7 of the diastole portion of the pressure cycle of the heart beat and just before the EGG peak that initiates each heart beat where the volume change is the lowest. For cardiac synchronized SIG-SBRT and SIG-SABR or lung tumors the 19 images are still taken during the exhale portions of the respiratory cycles but are delayed unless they also correspond to the diastole Regions 1, half of 6 and 7 of the cardiac cycle. This will inevitable spread the 19 kV projection image acquisitions over 2 or 3 or more respiratory cycles, correspondingly lowering the overall accuracy but still much better than previous systems that have to have margins that encompass all respiratory and cardiac motion that includes substantial damage to a lot of healthy tissue and bone.

Another alternate or additional feature of embodiments increases the frame rate of the kV images acquisition to 600 fps and lowers the dwell time for each focal spot to 1.7 ms for the multi-source kV e-Beam X-ray tube 208. This substantially lowers the acquisition time for the 19 kV projection images and speeds up the radiotherapy fraction delivery cycle to as high as 1.87 cycles per second. This means that the DTS image acquisition can be a short as one respiratory cycle (depending on synchronization with cardiac rates) so that motion tracking, MLC latency and treatment fraction delivery can be as short and as accurate as two respiratory cycles allows. This depends on several factors including the sufficient computer speeds required for fast DTS image reconstruction in the corresponding limited time, the DTS images still being of "tracking quality" even though the mAs from the e-Beam kV X-ray tube 208 will be corresponding less than when a 7 ms dwell time is used, and finally on the availability of a radiation hard, amorphous silicon X-ray imager that can operate at 600 fps.

Another alternate or additional feature of some embodiments is to use a full sized amorphous silicon flat panel portal imager, such as one 43×43 cm in active area, but only readout a reduced region-of-interest (ROI) so as to achieve or 600 fps or higher imaging rates.

Another alternate or additional feature of some embodiments may use the embodiments described above to track tumor motion in multiple other sites in the body during radiothearapy where motion management is a problem.

The following discussion now refers to a number of methods and method acts that may be performed. Although the method acts may be discussed in a certain order or illustrated in a flow chart as occurring in a particular order, no particular ordering is required unless specifically stated, or required because an act is dependent on another act being completed prior to the act being performed.

Figure 6:
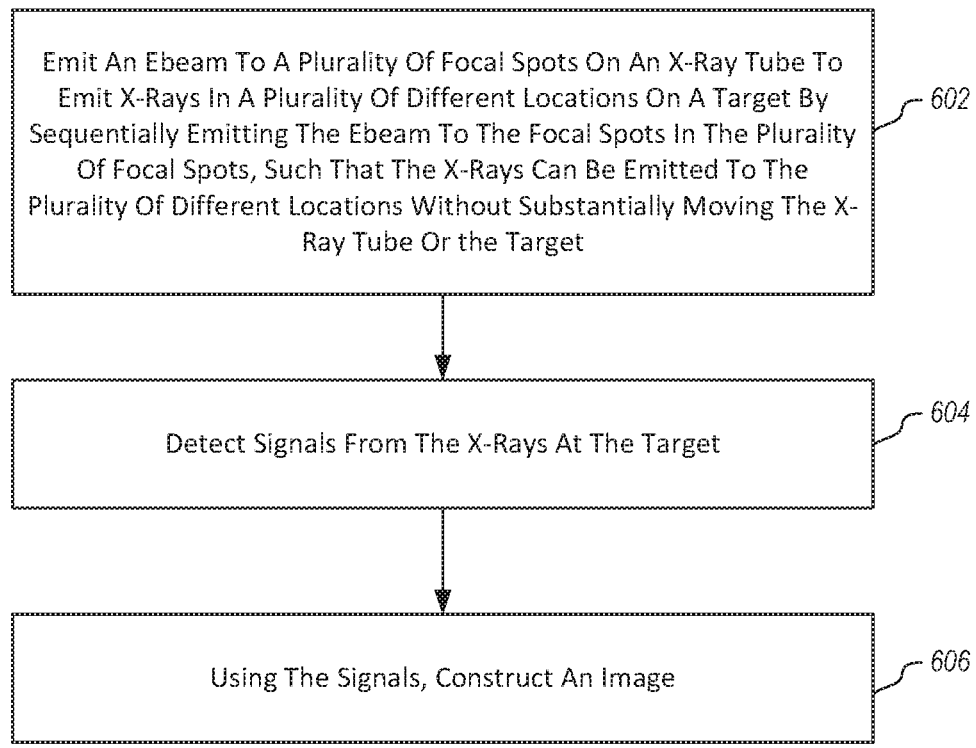
FIG. 6 illustrates a method of tracking tumors during radiotherapy.

Referring now to FIG. 6, a method 600 is illustrated. The method 600 includes acts for tracking tumors during radiotherapy for interleaving treatment pulses with imaging pulses. The method 600 includes emitting an ebeam to a plurality of focal spots on an x-ray tube to emit x-rays in a plurality of different locations on a target by sequentially emitting the x-rays to the focal spots in the plurality of focal spots, such that the x-rays can be emitted to the plurality of different locations without substantially moving the x-ray tube or the target (act 602). The method 600 further includes detecting signals from the x-rays at the target (act 604). Using the signals, an image is constructed (act 606).

The method 600 may be practiced where emitting an eBeam to a plurality of focal spots on an X-ray tube comprises emitting an eBeam to 19 spots on the X-ray tube.

The method 600 may be practiced where constructing the image comprises processing detected signals using one or more GPUs.

The method 600 may be practiced where the method is performed by sequentially emitting the X-rays to all the focal spots in one respiratory cycle of a patient being treated The method 600 may be practiced where emitting an eBeam to a plurality of focal spots on an X-ray tube to emit X-rays in a plurality of different locations on a target is synchronized with a cardiac cycle of a patient being treated.

The method 600 may be practiced where the method is performed to achieve an image acquisition rate of 600 fps.

The method 600 may be practiced where emitting X-rays comprises emitting X-rays of no more than 130 kV.

Figure 7:
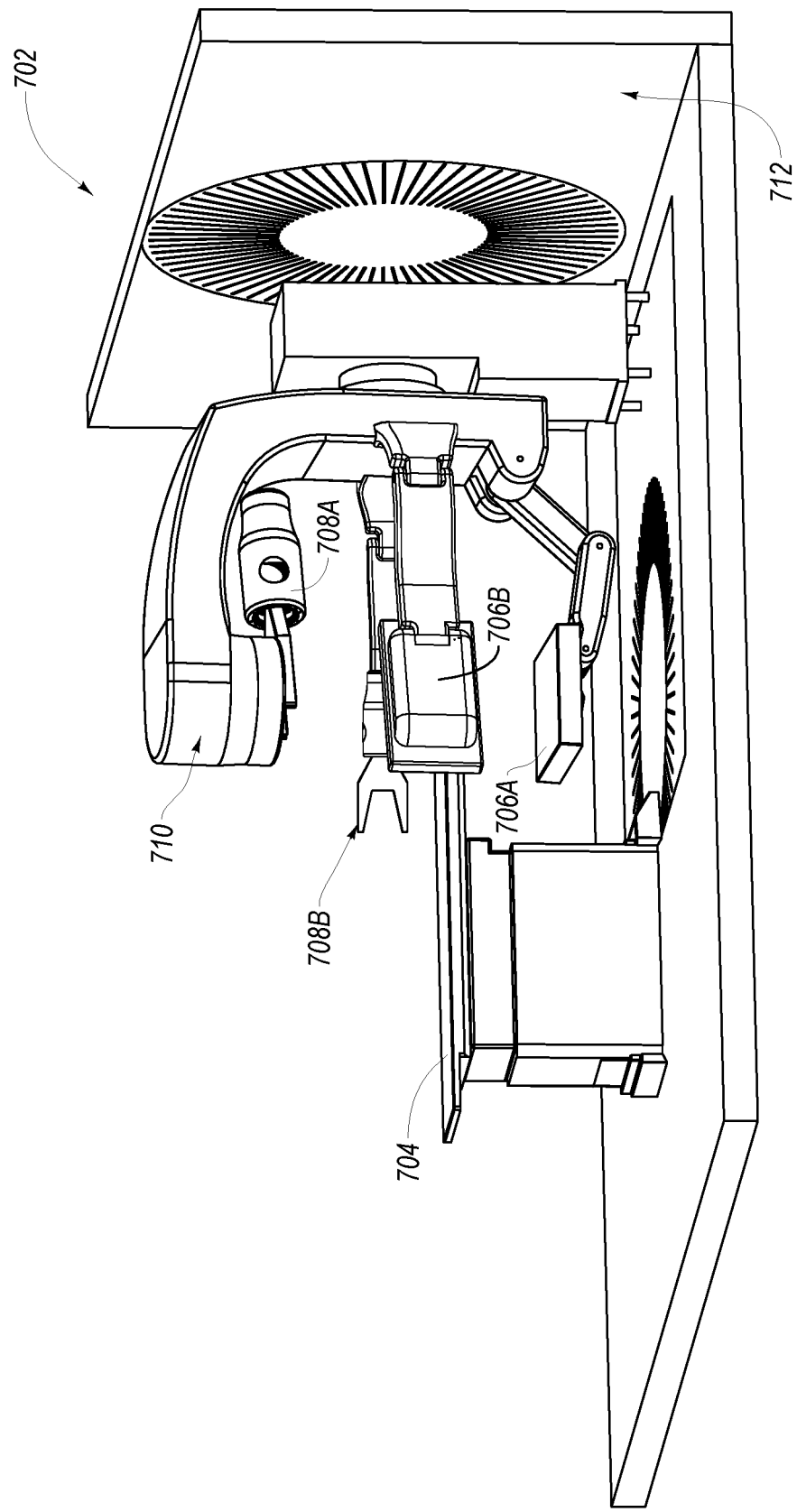
FIG. 7 illustrates an alternative example of a radiotherapy system.

Turning now to FIG. 7, a rotating C-arm MV linac radiotherapy system 702 is shown with a patient positioning support table 704. The radiotherapy system 702 includes a portal X-ray imager panel 706A that is placed opposite the gantry treatment head 710 to help monitor the patient and tumor positions for set up and during treatment. As with the embodiment of FIG. 2, the radiotherapy system 702 can be conceptualized as a standard MV portal imager but, turned upside down to convert it into a universal kV-MV portal imager. The system 702 also includes a multi-source X-ray tube 708A mounted directly under the MV linac gantry treatment head 710. A second (and potentially a third) multi-source X-ray tube 708B is also used in conjunction with a second portal X-ray imager panel 706B. These supplemental X-ray tubes and imager panels may be used to substantially reduce scanning time, while providing an overall clearer image.

One embodiment described herein includes a system for tracking biological features during radiotherapy. The system (e.g. 702 of FIG. 7) includes a first multisource scanning X-ray tube 708A that has multiple focal spots. The first X-ray tube 708A is configured to emit X-rays in multiple different locations on a first target (e.g. 706A) by sequentially emitting the X-rays to the focal spots in the plurality of focal spots. As such, the X-rays can be emitted to the different locations without substantially moving the first X-ray tube or the first target. As described above with reference to FIG. 3A-3D, the X-ray beam thus is focused successively on discrete targets and moved from target to target by steering the eBeam. X-rays are thus emitted at each of these targets and are directed by a collimator toward the flat panel image receptor (e.g. 706A).

The system further includes a first imager panel 706A configured to act as the first target for the first X-ray tube 708A. The first imager panel 706A receives the X-rays from the focal spots of the first X-ray tube 708A. The system also includes a second multisource scanning X-ray tube 708B that has multiple focal spots. The second X-ray tube 708B is configured to emit X-rays in multiple different locations on a second target by sequentially emitting the X-rays to the focal spots in the plurality of focal spots. Still further, the system includes a second imager panel 706B configured to act as the second target for the second X-ray tube, where the second imager panel 706B receives the X-rays from the focal spots of the second X-ray tube 708B. They system 702 also includes a tomosynthesis reconstruction module 712 configured to process output from the first and second imager panels to construct a unified two- or three-dimensional image that takes information from both the first and the second imager panels.

Thus, embodiments herein provide a real-time CT imaging system that can be mounted on a Radiotherapy gantry (e.g. 702) for tumor tracking. By placing either two, three or more Digital TomoSynthesis (DTS) systems on a radiotherapy gantry, CT images of the body can be obtained in a time of 0.25 seconds or less. The CT volume images may be formed in real-time using a graphics processing unit (GPU) system programmed to support a sparse view iterative reconstruction algorithm and an automatic image segmentation program. These programs and algorithms will be explained in greater detail below. The data from this system is then used to adjust the position of a multi-leaf collimator (MLC) in order to steer the therapy beam and shape as the tumor moves. The system 702 may have lower cost than MRI guided radiation therapy systems, and may further have improved performance including less interference with established clinical radiotherapy procedures.

The X-ray tomography system enables real time tumor tracking during radiotherapy with minimal interference with standard clinical equipment. In some embodiments, the multi-source X-ray tubes (e.g. 708A/708B) each have 19 focal spots that are placed below the multi-leaf collimator (MLC) of a radiotherapy system. By steering a focused electron beam (e-beam) on a series of 19 cooled tungsten targets in sequence, the system will provide a set of projection images that can be reconstructed into a two-dimensional (e.g. 20 cm×20 cm) DTS image or into a three-dimensional (e.g. 20 cm×20 cm×20 cm) digital tomosynthesis volume image that surrounds the radiation target. The projection X-rays from each X-ray tube are captured by respective kV-MV imagers (706A/706B) that can record portal MV images interlaced with the sequence of tomographic kV images.

Since the sources are positioned around the perimeter of the MLC, the resulting tomographic cross section images are aligned perpendicular to the axis of the therapy beam. This geometry is referred to herein as "Beam's eye view" imaging. By placing a second DTS system (i.e. 708B/706B) at right angles to the first (i.e. 708A/706A), dual-DTS CT volume images can be obtained using sparse view iterative reconstruction algorithms. CT image quality can be further improved by adding a third DTS system at an optimum angle relative to the two other DTS system. Such a triple-DTS system extends the capability of the overall system, including allowing tracking of low-contrast tumors in the abdomen and pelvis.

The CT images from dual- and triple-DTS are used to provide precise reference coordinates of a tumor surface for programming of the MLC, in real-time or substantially real-time. In some cases, a repetition rate of three or more volume images per second may be achieved with a spatial resolution of one millimeter or finer. This allows for detection of tumors in the abdomen and pelvis which are a more demanding site since tumors there typically have lower contrast and the body is substantially thicker. The dual-DTS system (or triple-DTS system) thus provides increased clarity and contrast in chest imaging and imaging of tumors in the abdomen. It also reduces motion related safety zones in treatment plans, thereby decreasing the volume of healthy tissue exposed to radiation.

Indeed, cancer is a leading cause of death in the United States. Radiotherapy is frequently employed for both its definitive and palliative treatment. Dosage for radiation is limited by the risk of toxicity to sensitive normal structures. Methods of reducing the volume of adjacent normal tissue irradiated as margin to avoid a geographic treatment failure are thus described herein. These methods reduce normal tissue injury. Accurate tumor tracking strategies will mitigate the need for an ITV margin. For example, a lower lobe tumor ITV margin may be as substantial as 20 mm or more in the craniocaudal direction, and will also limit PTV margin size. This reduction in the final target volume size will, at least in some embodiments, reduce dosages to critical structures such as the lungs and heart and thus improve patient outcomes.

As noted above, tumors in the abdomen and pelvis typically have low contrast and may be difficult to automatically segment using only BEV DTS due to loss of contrast and tomographic artifacts. Further, due to the greater thickness of the abdomen and pelvis compared to the air-filled chest, more X-ray photons are used to generate an image. In the embodiments herein, one or more additional multi-source X-ray scan tubes and image panels are mounted on or around the gantry. Then, CT volume images are reconstructed from the plurality of inputs.

Reconstruction may use iterative algorithms optimized for sparse view reconstruction and interior tomography. In one embodiment, the simultaneous algebraic reconstruction technique (SART) is used to reconstruct the output images. The images may be processed using SART or another algorithm running on a GPU processor. Using such an algorithm, 2X, 3X or more X-ray mAs may be used as required for body imaging. Identical or similar multi-source X-ray DTS tubes may be used for the additional views. These plural multi-source X-ray DTS tubes provide dual-DTS and triple-DTS, gaining either 2X or 3X more photons, respectively, with these configurations.

A single-DTS system produces DTS cross section images in planes through the treatment region that are transverse to the therapy beam (BEV). The single-DTS system (described above with reference to FIG. 2) implemented a unique kV multi-source electron beam (e-beam) X-ray tube that provided rapid switching of an X-ray focal spot in sequence from 19 target sites positioned along three sides of a square (as generally shown in FIGS. 3A-3D). This arrangement of focal spots nearly surrounds the MLC near the therapy radiation head.

A collimator system consisting of a tantalum plate with machined apertures just below the targets collimates the X-ray beams such that the universal kV-MV imager can receive each of the 19 projection images in sequence. Since the focal spots are offset, only ½ or less number of rows of pixels in the imager are exposed as the electron beam moves from one tungsten target to the next. The panel is exposed for 7 ms by X-rays from an 87 mA, 130 kV electron beam, directed onto an inclined, water-cooled tungsten target, focused to an effective spot size of 1.4 mm full width at half maximum. The beam is formed and steered using various methods.

The embodiments described herein can include multiple designs and forms. The system 702 may have a U-shaped opening large enough for the radiotherapy beam to pass through. The stationary targets support pulsed operation of an 87 mA beam, for example, with target water cooling. A unique feature of the kV-MV imagers 706A/706B is their ability to also record images from the therapy beam. This is feasible since the normal MV copper buildup plate can be placed on the back side of the imager, and a forward bias applied to clear a prior image from MV therapy beam exposure in a time interval of e.g. 75 msec, for high sensitivity kV imaging, that includes non-linear lag corrections.

As implemented herein, adding scan tubes to approximate the 180 degree range used for CT imaging, the system 702 can improve the image quality for abdomen, pelvis or other imaging using advanced sparse view and interior tomography CT iterative reconstruction algorithms. Single, dual, and triple DTS systems are advantageously low-cost, have minimal interference with standard radiotherapy procedures, and exact mechanical registration of the therapy beam and the image (Mill images are not fixed in space and may shift as ambient fields shift). Such DTS systems can provide highly accurate tumor tracking. The availability of a volume image simplifies automatic tumor segmentation.

Figure 8:
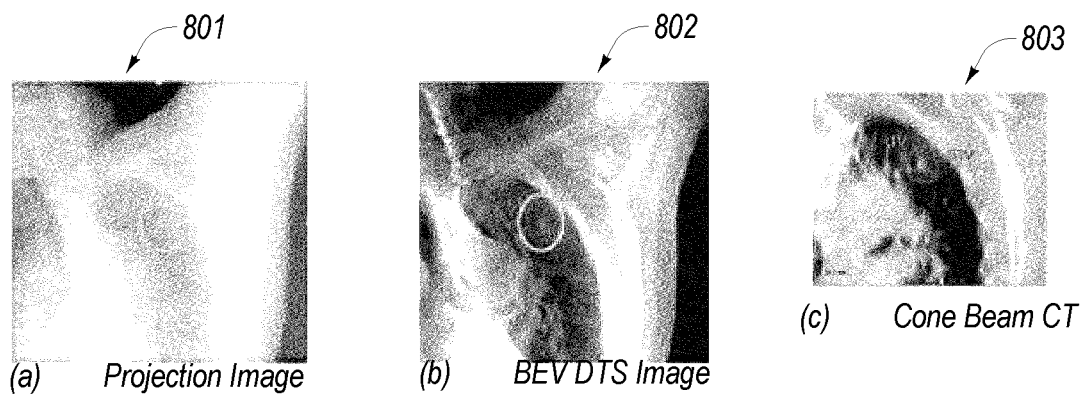
FIG. 8 illustrates example projection images.

For example, a single-DTS simulation using kV cone-beam CT projection images from a linac system is shown in FIG. 8. The left panel 801 is one frame from an 11 fps fluoro sequence of the lungs that cannot resolve the lesion, although some gross lung anatomy is visible. The central panel 802 is the BEV DTS image that was iteratively reconstructed using SART from the 19 cone beam CT projection images covering a 30 degree angle. Here, the lung cancer lesion is clearly resolved, providing sufficient quality for image guided radiotherapy. The right panel 803 is the cone beam CT slice image of this same view obtained from the 661 projection images obtained over a 60 s acquisition time at 11 fps. It should be noted that cone beam CT clearly shows the same lesion at higher contrast but with notably less resolution due to motion over the 1 min cone beam acquisition time. The net result was that with 3% (19/661=0.029) of the x-ray exposure and acquisition time of cone beam CT, the single DTS simulation gave tomosynthesis slice image approaching CT quality in the BEV direction. This imaging was repeated at more gantry rotation angles with similar results.

Figure 9:
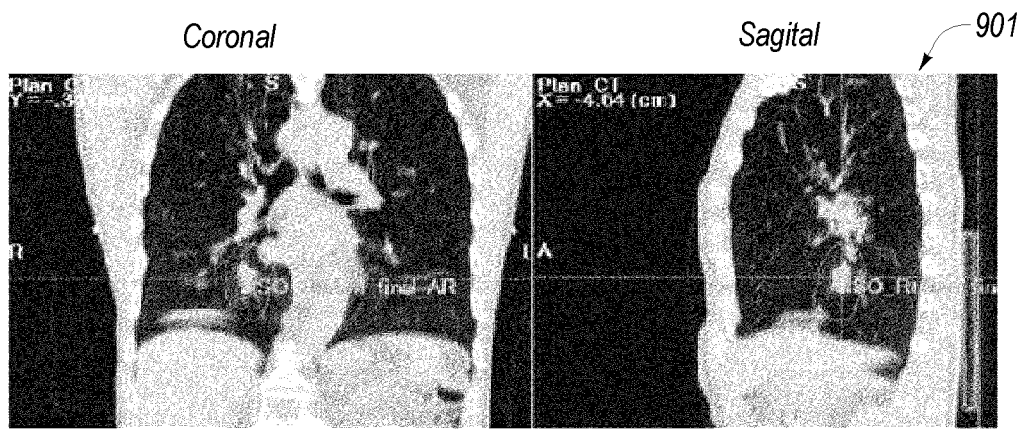
FIG. 9 illustrates alternative example projection images.
Figure 9:
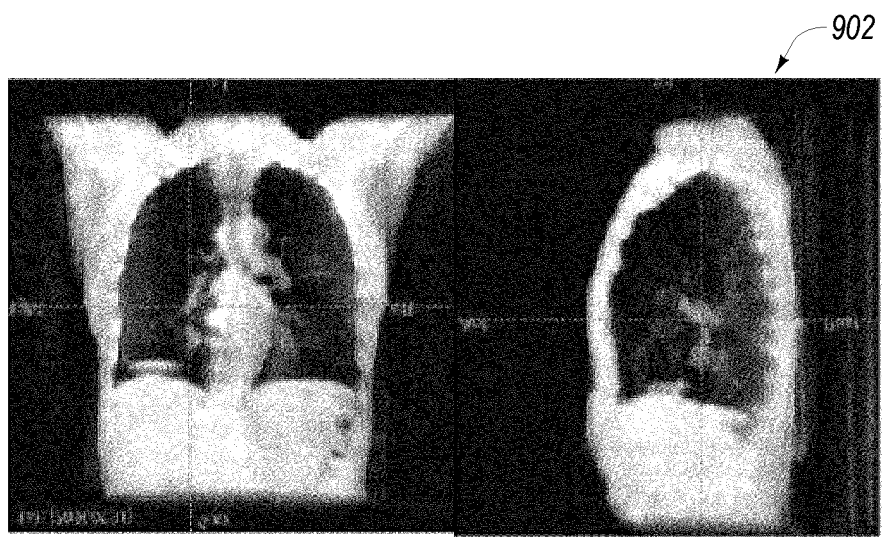

In the embodiments herein, 3D tomographic image quality is improved by adding a second and even a third DTS system in order to obtain full CT volume images while still preserving DTS's much lower x-ray exposure levels and fast data acquisition times. FIG. 9 shows an example of dual-DTS CT images of a lesion in the lower chest. The top row 901 shows the coronal and sagittal CT images with the very large treatment plan designed to accommodate the range of motion of this lesion. The bottom row 902 shows simulated dual-DTS images of the legion obtained by re-projections of the CT data according to geometry of the scan tubes (e.g. 38 sources) and reconstructed with a SART (or other) iterative algorithm.

At least in some embodiment, the following components are used: three multi-source scan tubes, a high voltage power supply (HVPS) with 3 outputs, three deflection coil systems, and a scan control computer. The electron beam is steered onto the tungsten targets using a beam tuning system consisting of trident wires for beam profile measurements. X-ray tuning may be performed using a pin hole collimator with 19 1-mm holes positioned such that a pin hole image is produced of the focal spot of each target on a Varian flat panel detector. The tuning program will then be adjusted to optimize the focus spot size, position, and ellipticity on each target. Over time, the tuning software may learn based on past use, and may be automated so that the multi-source X-ray tube will be able to self-calibrate at startup. Prior to X-ray tuning, the deflection and focusing system may be calibrated using three trident wires for beam profile measurements that are provided at the front of the MSXT chamber.

In addition to the above hardware, the iterative reconstruction algorithm may also be improved over time using feedback and machine learning techniques. GPUs may be used to implement selected advanced sparse views as well as interior tomography reconstruction algorithms. This may involve specialized coding of GPU cards with specialized programming languages. The new algorithms may be used in addition to or in conjunction with SART and SIRT algorithms. These algorithms may yield demonstrable improvements in dual- and triple-DTS image quality.

As noted above, the system 702 shown in FIG. 7 is a dual-DTS system. The first X-ray tube 708A in the dual-DTS system (as well as the first imager panel 706A) may be placed below a multi-leaf collimator (MLC) that is attached to a support structure of the system, while the second X-ray tube 708B (and second imager panel 706B) is placed at a right angle thereto. Alternatively, the first and second X-ray tubes 708A/708B may be positioned around the perimeter of the MLC. As such, the resulting tomographic cross section images are aligned perpendicular to the axis of a therapy beam. This provides "Beam's Eye View" imaging during tomosynthesis. The first and second imager panels may be kV-MV imager panels or other types of imager panels that are configured to record portal MV images interlaced with a sequence of tomographic kV images. Examples of such images are shown in FIGS. 8 and 9.

The tomosynthesis reconstruction module 712 may include computer hardware and/or software configured to implement a sparse view iterative reconstruction algorithm when generating the two- or three-dimensional image. The computer hardware and/or software of the tomosynthesis reconstruction module 712 may be located on or near the system 702, or may be located remotely. For instance, processing power, memory, data storage or other computer resources may be provided remotely via the cloud. The tomosynthesis reconstruction module 712 may include a plurality of processors or special purpose processors such as graphics processing units (GPUs) in order to speed up application of the sparse view iterative reconstruction algorithm.

The sparse view iterative reconstruction algorithm is applied to data received from the imager panels 706A/706B. The imager panels detect X-rays provided by the X-ray scanning tubes 708A/708B. The sparse view iterative reconstruction algorithm can stitch together information gathered by one, two, three or more imager panels to generate a single, two- or three-dimensional image or presentation. In some cases, the image may be displayed for view by doctors or other medical professionals. This display may be generated in real time by the tomosynthesis reconstruction module 712. The three-dimensional image provides clear images of biological features including, among other things, tumors. The tomosynthesis reconstruction module 712 may render or otherwise provide reference coordinates for a tumor surface, identifying where in the image (i.e. in the patient's body) the tumor appears. These reference coordinates for the tumor surface may then be applied as input to an MLC in real-time or in near real-time.

The tomosynthesis reconstruction module 712 may be configured to provide a repetition rate of at least three volume images per second. In some cases, the repetition rate may be higher or lower. Moreover, the tomosynthesis reconstruction module may be configured to provide at least 1-mm spatial resolution or, in some cases, sub-1-mm spatial resolution.

Although not shown in FIG. 7, the DTS system may include a third multisource scanning X-ray tube having a plurality of focal spots. The third X-ray tube is configured to emit X-rays in a plurality of different locations on a third target by sequentially emitting the X-rays to the focal spots in the plurality of focal spots. Such a DTS system would also include a third imager panel configured to act as the third target for the third X-ray tube. As such, the third imager panel receives the X-rays from the focal spots of the third X-ray tube. The tomosynthesis reconstruction module 712 then processes output from the first, second and third imager panels to construct a unified three-dimensional image that takes information from each of the first, the second and the third imager panels. It is further conceivable that four, five or more scanning X-ray tubes and imagers may be used if desired. Regardless of how many are used, the tomosynthesis reconstruction module 712 may be configured to combine the inputs from the imager panels into a unified three-dimensional image.

Each multisource X-ray tube may include a U-shaped head having the plurality of focal spots (as generally shown in FIGS. 3A-3D). In some embodiments, each multisource X-ray tube has 19 focal spots. Of course, it will be understood that substantially any number of focal spots may be used. Using a plurality of these multisource X-ray tubes can greatly improve CT image quality. Adding a third DTS system at an optimum angle extends the capability of the system to tracking low-contrast tumors in the abdomen, pelvis and other areas of the body.

Figure 10:
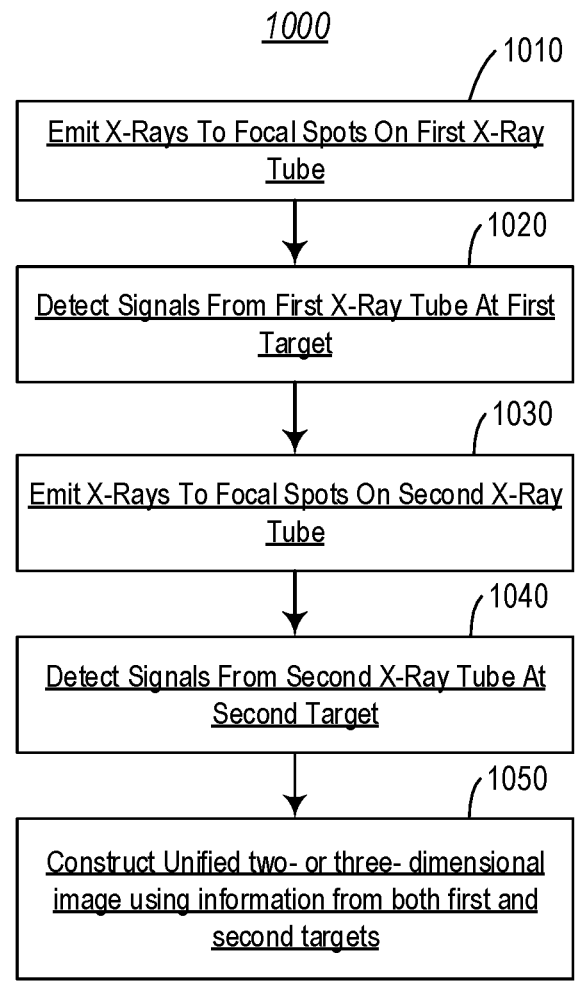
FIG. 10 illustrates an example method for providing real time tracking of a biological feature during radiotherapy.

Turning now to FIG. 10, a method 1000 is described for providing real time tracking of a biological feature during radiotherapy. The method includes emitting an eBeam to a plurality of focal spots on a first X-ray tube (e.g. 708A of FIG. 7) to emit X-rays in a plurality of different locations on a first target 706A by sequentially emitting the X-rays to the focal spots in the plurality of focal spots, such that the X-rays can be emitted to the plurality of different locations without substantially moving the first X-ray tube or the first target (1010). The method next includes detecting X-rays from the first X-ray tube at the first target (1020). The X-rays are detected at the first imager panel 706A (i.e. the target).

The method further includes emitting an eBeam to a plurality of focal spots on a second X-ray tube 708B to emit X-rays in a plurality of different locations on a second target 706B by sequentially emitting the X-rays to the focal spots in the plurality of focal spots (1030). The second imager panel 706B detects X-rays from the second X-ray tube (1040). The tomosynthesis reconstruction module 712 then constructs a unified three-dimensional image using information from both the first and the second targets (1050). In some cases, the second X-ray tube 708B and the second imager panel 706B are placed at a right angle to the first X-ray tube 708A and the first imager panel 706A. In cases where three X-ray tubes and imager panels are used, they may each be placed at appropriate angles relative to each other, in order to provide optimal scanning results.

The tomosynthesis reconstruction module 712 implements a reconstruction algorithm such as a sparse view iterative reconstruction algorithm to generate the two- or three-dimensional image. The image may provide or may include adjustment data for a multi-leaf collimator that adjusts a cross-section of a therapy beam to conform to the outline of the biological feature. The first, second and/or third X-ray tubes thus approximate a 180-degree range used in computerized tomography (CT) scans. In cases where a therapy beam is used to treat the tumor or other biological feature, the hardware and/or software of the tomosynthesis reconstruction module 712 may be used to record images from the therapy beam.

Accordingly, methods, systems and devices are described which provide real time tracking of a biological feature during radiotherapy. These methods, systems and devices provide high quality, real-time imaging and are much faster than traditional CT scans. Indeed, scans using the dual-DTS or triple-DTS systems described herein can be performed in under 15 seconds. This is a short enough time span that a patient should easily be able to hold their breath while the scan takes place. As one will note, this is much faster than a traditional CT scan which can take over a minute, during which time the patient will need to take multiple breaths thereby distorting the outputted image.

Furthermore, with dual-DTS and triple-DTS, the 3D image quality begins to approach CT image quality. This allows the 3D image to be used for treatment planning. Whereas traditional treatment planning is performed using scans obtained from a prior off-line CT study, or from a scan performed immediately before the therapy procedure, with real-time CT data provided by the dual- and triple-DTS systems described herein, treatment planning parameters may be adjusted in real-time to compensate for patient motion.

The concepts and features described herein may be embodied in other specific forms without departing from their spirit or descriptive characteristics. The described embodiments are to be considered in all respects only as illustrative and not restrictive. The scope of the disclosure is, therefore, indicated by the appended claims rather than by the foregoing description. All changes which come within the meaning and range of equivalency of the claims are to be embraced within their scope.

We claim:

1. A system comprising:
    a linac radiotherapy system comprising a treatment head to provide a treatment beam having a direction of propagation;
    an x-ray tube mounted to the linac radiotherapy system beneath the treatment head in the direction of propagation of the treatment beam, the x-ray tube comprising a U-shaped plurality of targets;
    an electron gun source to provide an electron beam; and
    a set of deflection coils to steer the electron beam to the U-shaped plurality of targets to generate x-rays.

2. The system of claim 1, further comprising:
    an imager to receive the x-rays.

3. The system of claim 2, the treatment beam having a path, the imager in the path of the treatment beam.

4. The system of claim 3, the linac radiotherapy system further comprising a multi-leaf collimator to shape the treatment beam, the x-ray tube to provide a plurality of sources of x-rays in response to the electron beam steered to the U-shaped plurality of targets, the plurality of sources positioned around a perimeter of the multi-leaf collimator.

5. The system of claim 1, the linac radiotherapy system further comprising a multi-leaf collimator to shape the treatment beam, the x-ray tube to provide a plurality of sources of x-rays in response to the electron beam steered to the U-shaped plurality of targets, the plurality of sources positioned around a perimeter of the multi-leaf collimator.

6. A system comprising:
    a linac radiotherapy system to provide a treatment beam having a path;
    an x-ray tube comprising a U-shaped plurality of targets to provide x-rays;
    an imager to receive the x-rays, the imager in the path of the treatment beam;
    an electron gun source to provide an electron beam; and
    a set of deflection coils to steer the electron beam to the U-shaped plurality of targets to generate the x-rays.

7. A system comprising:
    a linac radiotherapy system to provide a treatment beam, the linac radiotherapy system comprising a multi-leaf collimator to adjust a cross section of the treatment beam;
    an x-ray tube to provide a plurality of sources of x-rays positioned around a perimeter of the multi-leaf collimator, the x-ray tube comprising a U-shaped plurality of targets;
    an electron gun source to provide an electron beam; and
    a set of deflection coils to steer the electron beam to the U-shaped plurality of targets to generate the sources of x-rays.

8. The system of claim 7, the system to provide tomographic cross section images having a plane aligned perpendicular to the treatment beam.

* * * * *